US012485231B2

(12) United States Patent
Einwächter

(10) Patent No.: US 12,485,231 B2
(45) Date of Patent: Dec. 2, 2025

(54) CAP

(71) Applicant: Sanofi, Paris (FR)

(72) Inventor: Robin Einwächter, Frankfurt am Main (DE)

(73) Assignee: Sanofi, Paris (FR)

( * ) Notice: Subject to any disclaimer, the term of this patent is extended or adjusted under 35 U.S.C. 154(b) by 759 days.

(21) Appl. No.: 17/281,300

(22) PCT Filed: Sep. 27, 2019

(86) PCT No.: PCT/EP2019/076169
§ 371 (c)(1),
(2) Date: Mar. 30, 2021

(87) PCT Pub. No.: WO2020/069993
PCT Pub. Date: Apr. 9, 2020

(65) Prior Publication Data

US 2021/0402103 A1 Dec. 30, 2021

(30) Foreign Application Priority Data

Oct. 1, 2018 (EP) .................................... 18306288

(51) Int. Cl.
*A61M 5/32* (2006.01)

(52) U.S. Cl.
CPC ....... *A61M 5/3204* (2013.01); *A61M 2207/00* (2013.01)

(58) Field of Classification Search
CPC .............. A61M 5/3204; A61M 5/3202; A61M 5/3219; A61M 2005/3217; A61M 5/3205; A61M 2005/3215
See application file for complete search history.

(56) References Cited

U.S. PATENT DOCUMENTS

2012/0232491 A1 9/2012 Jennings
2016/0144132 A1* 5/2016 Scanlon .............. A61M 5/3202 604/192

(Continued)

FOREIGN PATENT DOCUMENTS

| | | | |
|---|---|---|---|
| EP | 3257536 | | 12/2017 |
| GB | 2465389 | A | 5/2010 |

(Continued)

OTHER PUBLICATIONS

PCT International Search Report and Written Opinion in International Application No. PCT/EP2019/076169, dated Nov. 5, 2019, 11 pages.

(Continued)

*Primary Examiner* — Michael J Tsai
*Assistant Examiner* — Neeraja Gollamudi
(74) *Attorney, Agent, or Firm* — Fish & Richardson P.C.

(57) ABSTRACT

A cap for an injection device includes an outer member and an inner member slidably received within the outer member and moveable between a first position and a second position; cooperating locking portions on the inner and outer members configured to secure the inner member relative to the outer member once moved into the second position; a clamping element extending inwardly from an arm of the inner member or a contact surface of the outer member; wherein, the cap is configured such that as the inner member is moved to the second position, the arm engages the contact surface causing the clamping element to move inwards to engage a body when disposed within the cap, and the cooperating locking portions engage and retain the inner member in the second position.

20 Claims, 7 Drawing Sheets

(56) References Cited

U.S. PATENT DOCUMENTS

| | | | | |
|---|---|---|---|---|
| 2016/0175539 | A1 | 6/2016 | Riedel et al. | |
| 2016/0317754 | A1 | 11/2016 | Schader | |
| 2017/0354789 | A1 | 12/2017 | Bendek | |
| 2017/0361030 | A1 * | 12/2017 | Moore | A61M 5/3204 |
| 2018/0185589 | A1 * | 7/2018 | Kemp | A61M 5/3204 |

FOREIGN PATENT DOCUMENTS

| | | | | |
|---|---|---|---|---|
| JP | 2009-538661 | A | 11/2009 | |
| JP | 2016-526996 | | 9/2016 | |
| JP | 2018-517519 | | 7/2018 | |
| TW | 201726194 | | 8/2017 | |
| WO | WO 2015/007857 | | 1/2015 | |
| WO | WO 2016/202916 | | 12/2016 | |
| WO | WO 2017/089266 | | 6/2017 | |
| WO | WO-2017089278 | A1 * | 6/2017 | A61M 5/20 |
| WO | WO 2018/104204 | | 6/2018 | |

OTHER PUBLICATIONS

PCT International Preliminary Report on Patentability in International Application No. PCT/EP2019/076169, dated Mar. 23, 2021, 8 pages.

* cited by examiner

CAP

CROSS REFERENCE TO RELATED APPLICATIONS

The present application is the national stage entry of International Patent Application No. PCT/EP2019/076169, filed on Sep. 27, 2019, and claims priority to Application No. EP18306288.4, filed on Oct. 1, 2018, the disclosures of which are incorporated herein by reference.

TECHNICAL FIELD

The present disclosure relates to a cap particularly but not exclusively for an injection device and a method of assembling said cap.

BACKGROUND

Injection devices, such as auto-injectors, are known in the art for dispensing a medicament to the injection site of a patient. Such injection devices typically comprise a body and a cap. A needle syringe is located in the body and is sometimes covered by a needle shield. The cap and needle shield are removably attached to the body to shield the needle of the needle syringe. To dispense the medicament, the cap and needle shield are first removed from the body to expose the needle. The needle is then inserted into the body of the patient at the injection site to dispense the medicament.

Conventional injection devices require a user to remove the cap and the needle shield separately to expose the needle in order to make the device ready for injection. It shall be appreciated that infirm patients such as the elderly or physically impaired may find removing the needle shield more difficult than removing the cap due to the small size of the needle shield making them difficult to handle.

SUMMARY

The present disclosure provides an improved cap.

According to the present disclosure, there is provided a cap for an injection device comprising an outer member; an inner member slidably received within the outer member and moveable between a first position and a second position in an axial direction of the cap; cooperating locking portions on the inner and outer members configured to secure the inner member relative to the outer member once moved into the second position; the inner member including an arm; the outer member comprising a contact surface on an inner wall thereof; a clamping element extending inwardly from the arm or the contact surface of the outer member, and being suitable for engaging a body when disposed within the cap; wherein the cap is configured such that as the inner member is moved to the second position, the arm engages the contact surface causing the clamping element to move inwards to engage a body when disposed within the cap, and the cooperating locking portions engage and retain the inner member in the second position.

The clamping element, contact surface and arms may be configured so that when the cap is on an injection device having a needle shield, the needle shield and the cap can be removed together which may help patients with reduced strength or dexterity, therefore separation of the needle shield from a housing may be made easier. Furthermore the removal of the cap and needle shield may be quicker and more efficient, as they are removed together in one action.

The locking portions may be configured to retain the inner member in the second position enabling the engagement between a needle shield and the cap to be established during assembly, rather than a user having to actuate the engagement.

Where the cap is used with an injection device with a syringe and a needle shield, the cap may be configured to prevent the syringe glass from breaking at a flange of the syringe due to a low holding force applied on the flange in comparison to some existing needle shield removal systems. Furthermore the cap may be configured so there is no active movement of a syringe as the clamping elements engage with a body or needle shield within the cap.

In some embodiments the clamping element may be provided on the arm and extend inwardly therefrom, and wherein as the arm engages the contact surface the arm can be caused to deflect inwards. However it can be appreciated that the clamping element may be provided on the contact surface and extend inwardly therefrom, and wherein as the arm engages the contact surface the contact surface may be caused to deflect inwards.

The movement of the clamping elements being inwards and the movement of the contact arms due to elastic material properties may enable a variety of sized bodies or needle shields to be engaged by the cap. Furthermore it may enable the cap to be put on an injection device having a needle shield without obstruction, but allow the cap to be removed with the needle shield due to engagement between the cap and the needle shield.

In some embodiments the first position may be an extended position in which the inner member partially extends from the outer member and the second position can be a retracted position in which the inner member may be further received within the outer member.

It may be that when the second position is configured to be a retracted position that an injection device including a cap will be easier to store and transport once assembled into the second position as the overall length of the device including a cap will be reduced. Pushing of the inner member further into the outer member to engage the locking portions may also be easier for assembly, or if actuated by a user then it may be easier for some users to push the inner member further into the outer member, especially if they are elderly or infirm or have reduced dexterity. They may push the inner member against a flat surface, such as a table.

In some embodiments the first position may be a retracted position in which the inner member is at least partially received within the outer member and the second position can be an extended position in which the inner member may be further extended from the outer member.

It may be that when the second position is configured to be an extended position that the assembly process is simplified as the action of pulling the inner member further from the outer member may be easier. Depending on the user it may also be easier for a user who has poor dexterity to pull the inner member from the outer member. The inner member may further include a tab or loop for a user to put around their fingers or another resilient protrusion and to hold on to the outer member to pull the inner member into the second position.

In some embodiments the inner wall of the outer member may have a slope to form the contact surface; in other embodiments the inner wall may comprise a protrusion or a thickening of the inner wall to form the contact surface. The contact surface may be shaped to taper towards a proximal end of the cap, however it can be appreciated that the contact surface may also taper towards a distal end of the cap.

The taper or slope of the contact surface may be configured to guide the clamping portions towards a body or needle shield within the cap. This may enable the elastic material properties of the arm to be exploited and may reduce the need for moving parts comprising mechanical connections such as joints or pivots.

In some embodiments the clamping element may be shaped to partially cut into or pierce a body or needle shield located inside the cap when the inner member is in the second position. The partial cut or piercing of a body or needle shield may provide a more robust engagement between the cap and the body or needle shield.

In some embodiments the clamping element is adapted to be frictionally engaged with a body or needle shield located inside the cap, when the inner member is in the second position.

The clamping element may be configured so that a non-metallic material can be used. This may reduce the overall weight of the cap and simplify the manufacturing process as parts could be made integral to one another, for example the arm and the clamping element may be integrally formed. Furthermore the clamping element may be configured to avoid the requirement for any sharp components within the cap.

In one embodiment the cap may have two or more arms which can be arranged to provide opposing forces inwards of the cap when the inner member is in a second position.

Where there are an even number of clamping elements, or clamping elements and non-moving supports it may be that there is no displacement of a body or needle shield inside the cap due to a radial force application.

In some embodiments the outer member or inner member, or both, may further comprise guide means for locating the inner member at a particular orientation within the outer member. For example the guide means may consist of, but not be limited to, tracks, grooves, ridges or channels.

The guide means may be configured to at least partially receive one of the arms which may reduce the overall diameter and therefore size of the cap. The guide means may be configured to locate the inner member at a particular orientation within the outer member; this may mean that a reduced number of clamping elements, arms and contact surfaces are required internally in the cap as specific components can be aligned such as the arm and the contact surface. The sliding motion of moving from the first position to the second position may also be improved by the configuration of the guide means.

In some embodiments there is an injection device comprising, a housing, a syringe having a needle at one end, and a needle shield. The needle shield is disposed within a cap wherein the cap and the needle shield are removed from the injection device simultaneously when the cap is in a second position. The syringe may also contain a medicament. The injection device may also be an auto injector.

It can be appreciated that a method of assembling an injection device including the cap as described above may comprise the following steps: insert a syringe into the injection device, the syringe having a needle and a needle shield covering the needle, fit the cap to the injection device such that it substantially covers the needle shield, slide the inner member of the cap relative to the outer member from a first position to a second position, the clamping element gripping the needle shield such that removal of the outer member also removes the needle shield, engage the cooperating locking portions on the inner and outer member to retain the cap in the second position.

In some embodiments the inner member may further comprise at least one non-moving support arm arranged on the inner member to provide an opposing force to that created by the clamping element when the device is in a second position. The opposing force may be towards the central axis of the cap. This non-moving support can reduce the number of moving parts in the cap and simplify the manufacturing process. A non-moving support may also not require a contact surface and therefore there would be less material required to produce the cap.

These and other aspects will be apparent from and elucidated with reference to the embodiments described hereinafter.

BRIEF DESCRIPTION OF THE FIGURES

Embodiments will now be described, by way of example only, with reference to the accompanying drawings, in which.

DETAILED DESCRIPTION

Figure 1A:
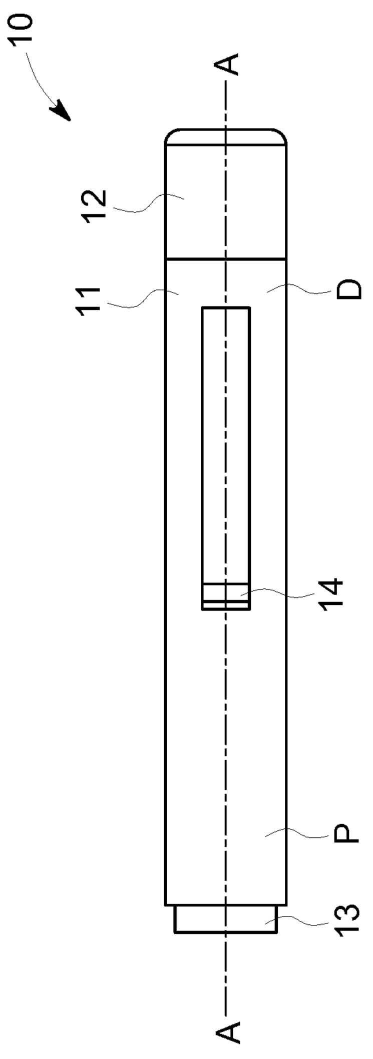
FIG. 1A is a schematic side view of an auto-injector with a cap attached to a housing of the auto-injector.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
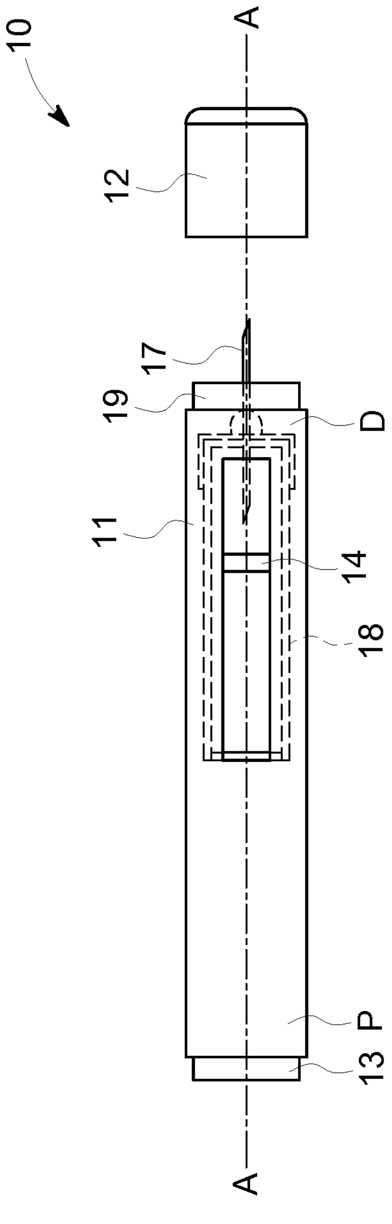
FIG. 1B is a schematic side view of the auto-injector of FIG. 1A, with the cap removed from the housing.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
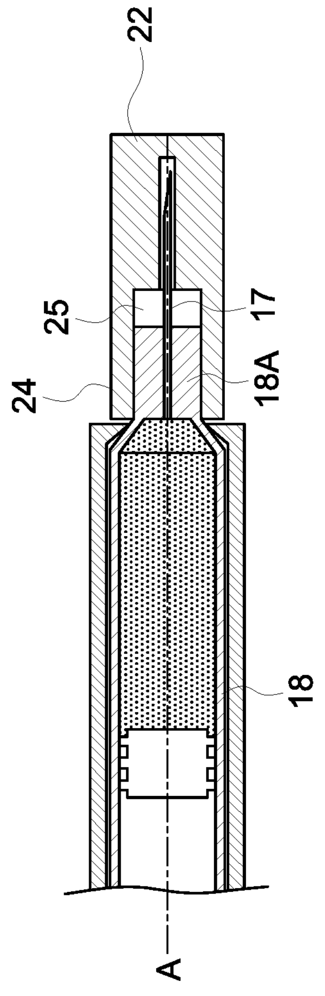
FIG. 2 is a close-up schematic cross-sectional side view of a needle shield of an auto-injector.

Referring now to FIG. 2 an injection device 10 can further comprise a needle shield 22. The needle shield 22 comprises a body 24 of impermeable material with a recess 25 in the proximal end of the body 24. The recess 25 is configured to receive the needle hub 18A and the needle 17 such that the needle 17 is shielded by the body 24. The inside surface of the body 24 and the outside surface of the needle hub 18A frictionally engage to seal the recess 25 to prevent the ingress of air into the recess 25. Thus, the needle 17 is kept sterile when the cap 12 is attached to the housing 11.

Figure 3:
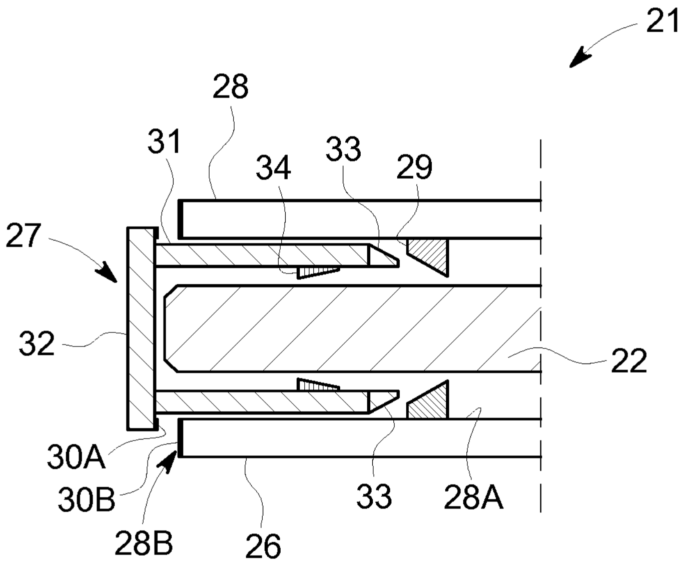
FIG. 3 is a close-up schematic cross-sectional side view of a cap according to a first embodiment, wherein the inner member is in a first position.
Figure 4:
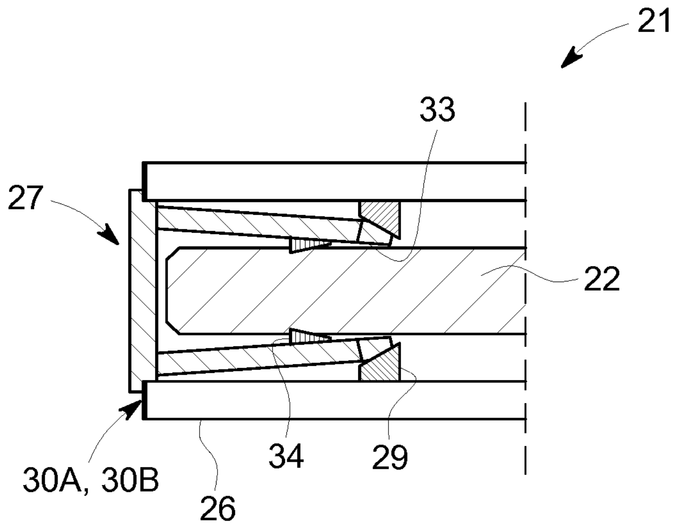
FIG. 4 is a close-up schematic cross-sectional side view of FIG. 3, wherein the inner member is in a second position.

It can be advantageous for the cap and the needle shield to be removed simultaneously which may make removal of the cap and needle shield easier for a user. FIGS. 3 and 4 show a cap according to a first embodiment. The cap 21 can be used with an injection device 10 such as those shown in FIGS. 1A to 2 replacing cap 12. The needle shield 22 is located inside the cap 21.

The cap 21 consists of an outer member 26 and an inner member 27. The inner member is slidably located within the outer member. The term "within" in relation to this application is intended to mean substantially within, at least a portion of the inner member is within the outer member. The cap also has a first and second position, where the first position can be an extended position in which the inner member 27 partially extends from the outer member 26 and the second position can be a retracted position in which the inner member 27 may be further received within the outer member 26.

The outer member comprises an outer member wall 28 with an inner face 28A and an end face 28B. The outer member wall 28 is integrally formed at its inner face 28A with a contact surface 29, however it can be appreciated that the contact surface may not be integrally formed. The contact surface 29 is located towards the proximal end of the outer member 26 and is substantially continuous throughout the inner face of the outer member wall 28A, tapering towards the proximal end of the injector. It can be appreciated however that the contact surface may not be continuous.

The inner member 27 has two arms 31 and an inner member end 32. The arms 31 are positioned at a pitch diameter smaller than the outer member wall 28 so that the inner member can slidably fit within the outer member. The inner member end 32 has a diameter larger than the outer member wall so that the inner member is not fully received within the outer member wall, however it can be envisaged that the inner member could be fully received within the outer member. The arms 31 have a shaped end 33 which engages with the contact surface 29 as the inner member is moved to the second position. The shaped ends 33 may be wedge shaped but it can be appreciated that they can be any shape which would cause the arms to be urged towards the central axis of the needle shield by the contact surface 29 when the inner member 27 is pushed into the outer member 26.

In some embodiments, and where there is more than one arm 31 they can be referred to as deflectable arms due to the deflection they experience as they are driven into the contact surface 29.

Clamping elements 34 are located on the inside of the arms 31 and are shaped to engage with the needle shield 22 when the inner member is in the second position. The clamping elements 34 are urged into the needle shield by the movement of the shaped end 33 guided by contact surface 29. This forced guidance creates a friction lock between the clamping elements 34 and needle shield 22, however it can be appreciated that the clamping elements may be shaped to a point to pierce or cut into the needle shield to form a lock.

The inner member and the outer member comprise cooperative locking portions 30A and 30B respectively for locking the inner member in a second position. The inner member, needle shield and outer member can then be removed as one component.

A cap 21 for an injection device is assembled by a method comprising the following steps. Slide the inner member 27 relative to the outer member from a first position to a second position, thus urging the arms 31 against the contact surface 29 and towards the needle shield. The clamping elements are also driven towards a central axis of the cap and they grip the needle shield such that removal of the outer member also removes the needle shield. Engage the cooperating locking portions 30A, 30B on the inner and outer member to retain the cap 21 in the second position.

Figure 5:
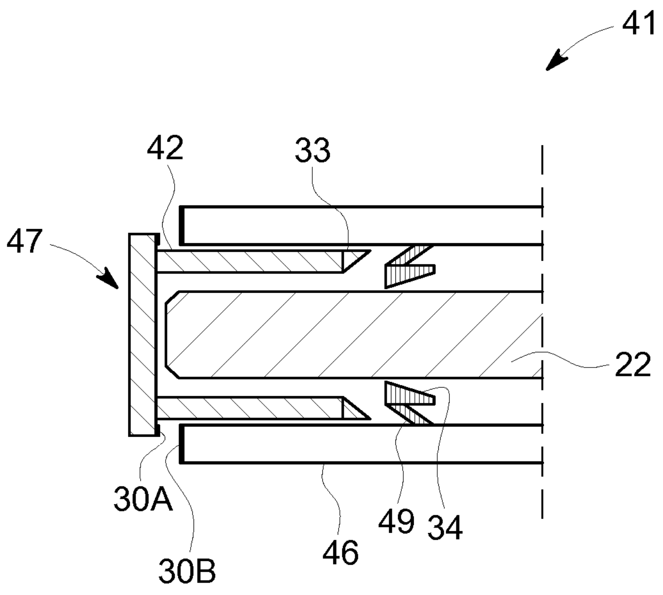
FIG. 5 is a close-up schematic cross-sectional side view of a cap according to a second embodiment, wherein the inner member is in a first position.
Figure 6:
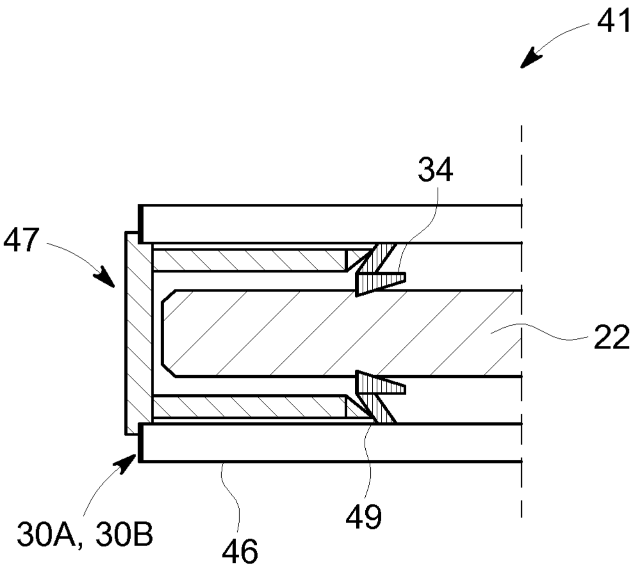
FIG. 6 is a close-up schematic cross-sectional side view of FIG. 5, wherein the inner member is in a second position.

Referring to FIGS. 5 and 6, a cap 41 according to a second embodiment is shown. The cap 41 has similar features to the cap 21 described above in relation to FIGS. 3 and 4 with like features retaining the same reference numerals. A difference is that the clamping elements 34 are located on the contact surface 49 of the outer member 46 as opposed to the inner member as in the first embodiment. The inner member 47 has one continuous arm 42 which is adapted to engage with the contact surface 49. In this embodiment the contact surface is deflected towards the central axis of the cap urging the clamping elements into the needle shield as the inner member is moved from the first position into the second position.

Figure 7:
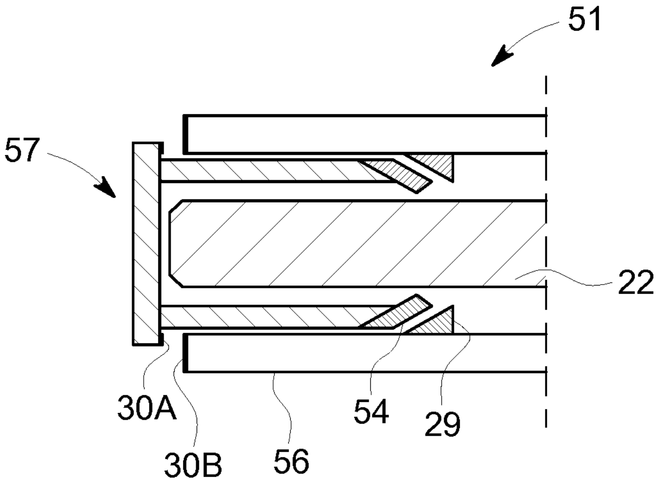
FIG. 7 is a close-up schematic cross-sectional side view of a cap according to a third embodiment, wherein the inner member is in a first position.
Figure 8:
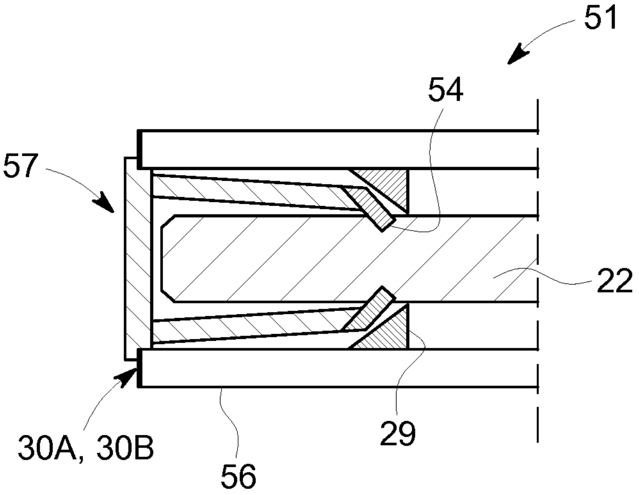
FIG. 8 is a close-up schematic cross-sectional side view of FIG. 7, wherein the inner member is in a second position.

Referring to FIGS. 7 and 8, a cap 51 according to a third embodiment is shown. The cap 51 has similar features to the cap 21 described above in relation to FIGS. 3 and 4 with like features retaining the same reference numerals. A difference is that the shaped ends 33 are replaced with clamping elements 54. The contact surface 29 forces the clamping elements 34 into the needle shield 22 as the inner member 57 is pushed into the outer member 56 (from a first position to a second position).

Figure 9:
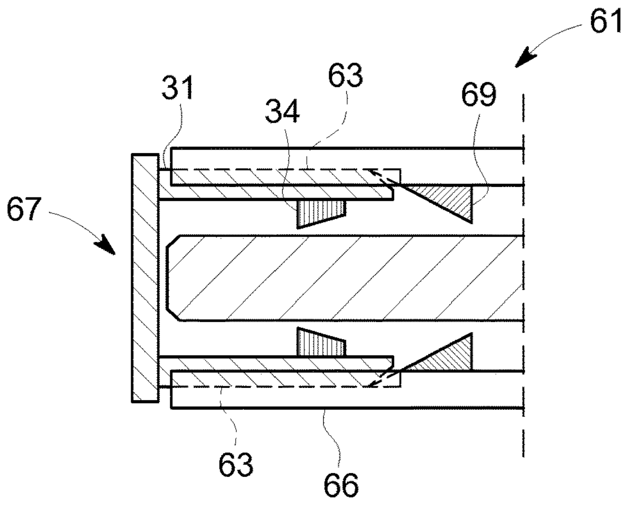
FIG. 9 is a close-up schematic cross-sectional side view of a cap according to a fourth embodiment, wherein the inner member is in a first position.
Figure 10:
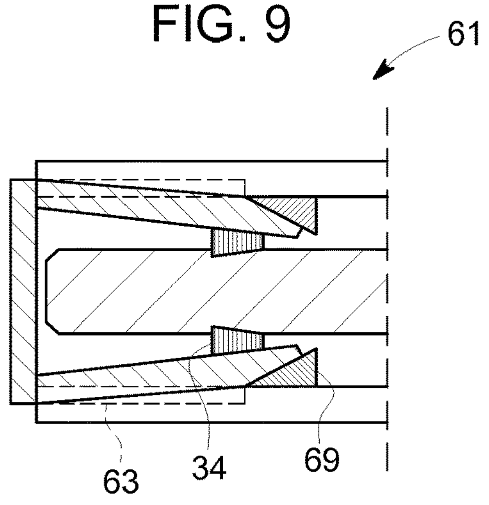
FIG. 10 is a close-up schematic cross-sectional side view of FIG. 9, wherein the inner member is in a second position.
Figure 11:
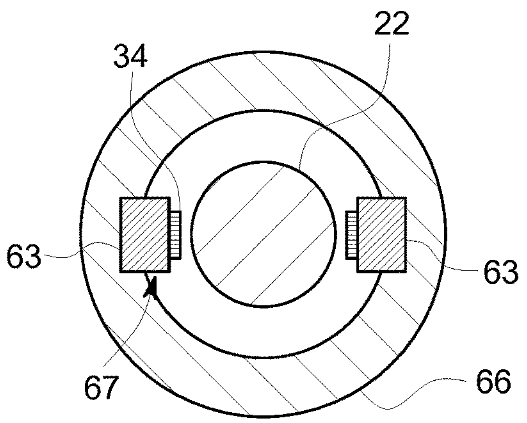
FIG. 11 is a close-up schematic cross-sectional plan view of FIG. 9 wherein the inner member is in a first position.

Referring to FIGS. 9 to 11, a cap 61 according to a fourth embodiment is shown. The cap 61 of the auto-injector of the fourth embodiment has similar features to the cap 21 described above in relation to FIGS. 3 and 4, with like features retaining the same reference numerals. A difference is that the contact surface 29 is not continuous throughout the inner face of the outer member but consists of at least one tapered protrusion 69. To ensure arms 31 and clamping elements 34 are aligned with the respective tapered protrusion forming the contact surface 29, the outer member 66 comprises guide means 63 to locate the respective inner member wall. The outer member 66 and tapered protrusion 69 of the fourth embodiment can also be used with the clamping elements 54 of the third embodiment.

The guide means 63 may consist of but not be limited to tracks, grooves, ridges or channels for locating the inner member 67 within the outer member 66.

Figure 12:
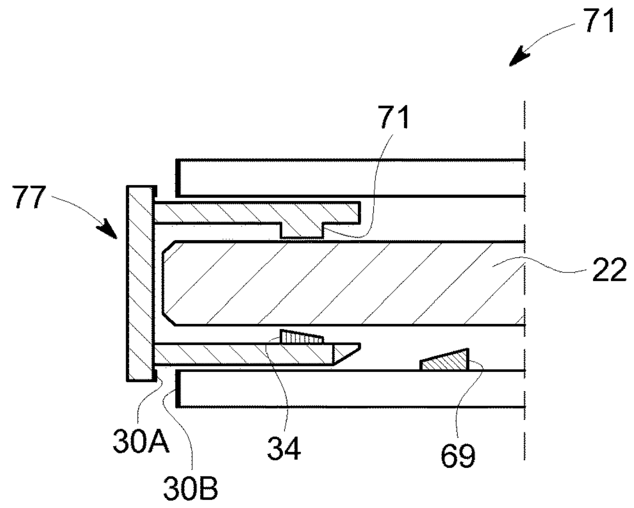
FIG. 12 is a close-up schematic cross-sectional side view of a cap according to a fifth embodiment, wherein the inner member is in a first position.

Referring to FIG. 12 a cap 71 according to a fifth embodiment is shown. The cap 71 of the fifth embodiment has similar features to the cap 21 described above in relation to FIGS. 3 and 4, with like features retaining the same reference numerals. A difference is that the inner member further comprises at least one non-moving support 74 arranged on the inner member 77 to provide an opposing force to that created by the clamping element 34 when the device is in a second position. The opposing force may be towards the central axis of the needle shield.

Figure 13:
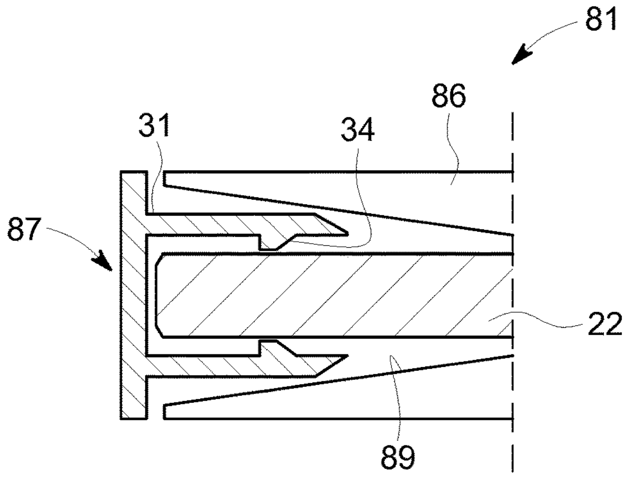
FIG. 13 is a close-up schematic cross-sectional side view of a cap according to a sixth embodiment, wherein the inner member is in a first position.

Referring to FIG. 13 a cap 81 according to a sixth embodiment is shown. The cap 81 of the sixth embodiment has similar features to the cap 21 described above in relation to FIGS. 3 and 4, with like features retaining the same reference numerals. A difference is that the outer member 86 has a thickening or slope to form the contact surface 89. The thickening of the contact surface tapers to a distal end of the cap. It can be appreciated that the thickening may be hollow, or may not be continuous throughout the axial length of the outer member. The clamping elements 34 and arm 31 are also integrally formed of the same material, which can be true of other embodiments previously described.

Figure 14:
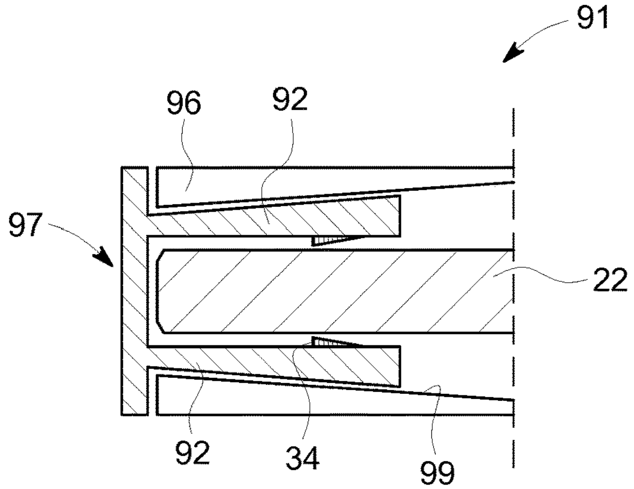
FIG. 14 is a close-up schematic cross-sectional side view of a cap according to a seventh embodiment, wherein the inner member is in a first position.

Referring to FIG. 14 a cap 91 according to a seventh embodiment is shown. The cap 91 of the seventh embodiment has similar features to the cap 21 described above in relation to FIGS. 3 and 4, with like features retaining the same reference numerals. A difference is that the outer member 96 has a thickening or sloped walls as in the sixth embodiment to form the contact surface 99 however the contact surface is tapered towards a proximal end of the cap. It can be appreciated that the thickening may be hollow, or may not be continuous throughout the axial length of the outer member. In this embodiment the first position may be a retracted position in which the inner member 97 is at least partially received within the outer member 96 and the second position can be an extended position in which the inner member may be further extended from the outer member. The arms 92 engaging with the contact surface 99, causing them to move axially inwards, urging the clamping elements 34 into the needle shield 22 as the inner member moves from a first position to a second position. Cooperative locking portions 30A and 30B (not shown in FIG. 14) are then engaged fixing the inner member 97 to the outer member 96, fixing the clamping elements in position with the needle shield, wherein removal of the cap also removes the needle shield 22.

Any of the above described embodiments may consist of a non-moving support as described above in a fifth embodiment. They may also include an enhanced gripping surface on the inner member or on the cap for manual actuation.

Any of the above described embodiments may consist of two oppositely located clamping elements to ensure radial force application on the needle shield. It can be envisaged that there would be more than two clamping elements oppositely located. There may also be three or more equally circumferentially spaced clamping elements to exert a radial force application on the needle shield.

In the above described embodiments, cooperating locking portions 30A and 30B may be clip holes located on the outer member and the inner member is adapted to be retained by the clip connection via clip hooks. However, in an alternative embodiment (not shown), the clip holes may be located on the inner member and the cap outer member may be adapted to be retained by the clip connection via clip hooks. Furthermore a series of complimentary clip hooks and clip loops may be located on each of the outer member and inner member adapted to engage with each other to retain the inner member once in the second position. Alternative cooperating locking portions may be used in place of a clip hook and clip hole connector, for example but not limited to, an adhesive, a friction lock, or a Velcro type hook and loop connector. One example of a friction lock is where the configuration of the inner and outer member causes them to frictionally engage one another when the inner member is moved relative to the outer member and into the second position. The frictional engagement is such that the inner member is locked to the outer member. In one embodiment, the clamping elements may be adapted to exert sufficient frictional force on the needle shield to prevent the inner member and outer member from coming apart once in the second position. Any surface of the clamping element, the inner member wall, the arm or contact surface can be made of, or coated with a high friction material.

The terms “drug” or “medicament” are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient (“API”), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or “drug container” adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms “analogue” and “derivative” refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as “insulin receptor ligands”. In particular, the term “derivative” refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term “antibody”, as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms “fragment” or “antibody fragment” refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A cap for an injection device, the cap comprising:

an outer member comprising a contact surface on an inner wall thereof;

an inner member slidably received within the outer member and axially moveable relative to the outer member between a first position and a second position in an axial direction of the cap, the inner member comprising an arm;

cooperating locking portions on the inner and outer members configured to secure the inner member relative to the outer member once moved into the second position; and a clamping element extending inwardly from the arm or the contact surface of the outer member, and being suitable for engaging a body when disposed within the cap, wherein the cap is configured such that as the inner member is moved relative to the outer member to the second position, the arm engages the contact surface causing the clamping element to move inwards to engage the body when disposed within the cap, and the cooperating locking portions engage and retain the inner member in the second position, and wherein the cap is removeable from the injection device.

2. The cap according to claim 1, wherein the clamping element is provided on the arm and extends inwardly therefrom, and wherein as the arm engages the contact surface the arm is caused to deflect inwards.

3. The cap according to claim 1, wherein the clamping element is provided on the contact surface and extends inwardly therefrom, and wherein as the arm engages the contact surface the contact surface is caused to deflect inwards.

4. The cap according to claim 1, wherein the first position is an extended position in which the inner member partially extends from the outer member and the second position is a retracted position in which the inner member is further received within the outer member.

5. The cap according to claim 1, wherein the first position is a retracted position in which the inner member is at least partially received within the outer member and the second position is an extended position in which the inner member is further extended from the outer member.

6. The cap according to claim 1, wherein the inner wall of the outer member has a slope to form the contact surface.

7. The cap according to claim 1, wherein the inner wall of the outer member comprises a protrusion to form the contact surface.

8. The cap according to claim 1, wherein the contact surface is shaped to taper towards a proximal end of the cap.

9. The cap according to claim 1, wherein the contact surface is shaped to taper towards a distal end of the cap.

10. The cap according to claim 1, wherein the clamping element is shaped to partially cut into the body located inside the cap when the inner member is in the second position.

11. The cap according to claim 1, wherein the clamping element is adapted to be frictionally engaged with the body located inside the cap when the inner member is in the second position.

12. The cap according to claim 1, wherein the inner member comprises two or more arms arranged to provide opposing forces inwards of the cap when the inner member is in the second position, the two or more arms comprising the arm.

13. The cap according to claim 12, wherein the two or more arms are equally circumferentially spaced.

14. The cap according to claim 1, wherein the cooperating locking portions comprise clip holes located on the outer member.

15. The cap according to claim 14, wherein the inner member further comprises clip hooks adapted to be retained by the clip holes.

16. The cap according to claim 1, wherein the cooperating locking portions comprise clip holes located on the inner member.

17. The cap according to claim 16, wherein the outer member further comprises clip hooks adapted to be retained by the clip holes.

18. An injection device comprising:

a cap comprising:

an outer member comprising a contact surface on an inner wall thereof, an inner member slidably received within the outer member and axially moveable relative to the outer member between a first position and a second position in an axial direction of the cap, the inner member comprising an arm, cooperating locking portions on the inner and outer members configured to secure the inner member relative to the outer member once moved into the second position, and a clamping element extending inwardly from the arm or the contact surface of the outer member, and being suitable for engaging a body when disposed within the cap, wherein the cap is configured such that as the inner member is moved relative to the outer member to the second position, the arm engages the contact surface causing the clamping element to move inwards to engage the body when disposed within the cap, and the cooperating locking portions engage and retain the inner member in the second position, and the cap is removeable from the injection device; and a housing;

a syringe, having a needle at one end; and a needle shield, being disposed within the cap, wherein the cap and the needle shield are removed from the injection device simultaneously when the cap is in the second position.

19. The injection device according to claim 18, wherein the syringe contains a medicament.

20. A method of assembling an injection device, the method comprising:

inserting a syringe into the injection device, the syringe having a needle and a needle shield covering the needle;

fitting a cap to the injection device such that the cap substantially covers the needle shield, the cap comprising:

an outer member comprising a contact surface on an inner wall thereof;

an inner member slidably received within the outer member and axially moveable relative to the outer member between a first position and a second position in an axial direction of the cap, the inner member comprising an arm;

cooperating locking portions on the inner and outer members configured to secure the inner member relative to the outer member once moved into the second position; and a clamping element extending inwardly from the arm or the contact surface of the outer member, and being suitable for engaging a body when disposed within the cap;

sliding the inner member of the cap relative to the outer member of the cap from the first position to the second position such that the arm engages the contact surface causing the clamping element to move inwards to engage the body, the clamping element of the cap gripping the needle shield such that removal of the outer member also removes the needle shield; and engaging the cooperating locking portions on the inner and outer members to retain the cap in the second position, wherein the cap is removeable from the injection device.

* * * * *